United States Patent
Werle et al.

(10) Patent No.: US 6,500,466 B2
(45) Date of Patent: *Dec. 31, 2002

(54) CHLORHEXIDINE FORMULATIONS, NEW CHLORHEXIDINE SALTS, SOLUTIONS CONTAINING THESE AND THEIR USE

(75) Inventors: Peter Werle, Gelnhausen (DE); Friedhelm Merz, Nierstein (DE); Judith N. Jørgensen, Østervang (DK); Martin Trageser, Gelnhausen (DE)

(73) Assignee: Degussa AG, Dusseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 93 days.

(21) Appl. No.: 09/458,717

(22) Filed: Dec. 13, 1999

(65) Prior Publication Data

US 2002/0018814 A1 Feb. 14, 2002

(30) Foreign Application Priority Data

Dec. 11, 1998 (DE) .......................... 198 57 151

(51) Int. Cl.⁷ .......................... A01N 59/08; A61K 33/14
(52) U.S. Cl. .......................... 424/661; 424/400; 514/557
(58) Field of Search .......................... 424/661, 400; 514/557

(56) References Cited

U.S. PATENT DOCUMENTS 5,565,487 A * 10/1996 Yu et al. .......................... 514/460
6,051,609 A * 4/2000 Yu et al. .......................... 514/557

FOREIGN PATENT DOCUMENTS

| EP | 0 181 161 A2 | | 5/1986 |
| EP | 0 200 607 A1 | | 11/1986 |
| FR | 2 752 731 A1 | | 3/1998 |
| WO | WO 90/10434 | * | 9/1990 |
| WO | WO 98/46217 | | 10/1998 |

* cited by examiner

*Primary Examiner*—Thurman K. Page
*Assistant Examiner*—Liliana Di Nola-Baron
(74) *Attorney, Agent, or Firm*—Pillsbury Winthrop LLP

(57) ABSTRACT

Powdered mixtures of chlorhexidine base with selected sugar acids or lactones from the group gluconic acid or gluconolactone, lactobionic acid (I), D-galactono-γ-lactone (II), L-mannono-γ-lactone (III), D-(−)-gulono-γ-lactone (IV), D-(+)-galacturonic acid (V) and α-D-heptaglucono-γ-lactone (VI). The formulations have extraordinary storage stability. New chlorhexidine salts with sugar acid anions based on (I) to (VI) and aqueous solutions of these are also described. The formulations, solutions and pure salts are used as disinfectants and to prepare disinfectants.

6 Claims, 2 Drawing Sheets

CHLORHEXIDINE FORMULATIONS, NEW CHLORHEXIDINE SALTS, SOLUTIONS CONTAINING THESE AND THEIR USE

CROSS-REFERENCE TO RELATED APPLICATION

This application is based on German Application DE 198 57151.8, filed Dec. 11, 1998, which disclosure is incorporated herein by reference.

FIELD OF THE INVENTION

The invention provides formulations which contain chlorhexidine base which can be converted into aqueous solutions of chlorhexidine salts. The invention is also directed to these solutions and the new chlorhexidine salts on which they are based. The formulations, solutions and salts can be used as disinfectants and to prepare disinfectants.

BACKGROUND OF THE INVENTION

Chlorhexidine, the formal chemical name for which is 1,1'-hexamethylene-bis-[5,4-chlorophenyl]-biguanide, is a strongly basic substance with a very low solubility in water. Sparingly water-soluble salts are produced by reacting the chlorhexidine base with a number of acids. Chlorhexidine base and, in particular, its water-soluble salt with D(+)-gluconic acid [CAS-No. 526-95-4] are important antibacterial substances and are used in both the human and animal sectors. The low toxicity and general compatibility with cationic and anionic detergents must be stressed. Chlorhexidine digluconate is provided as a 20% aqueous solution and is currently the only commercially available water-soluble form of the base. Liquid formulations of chlorhexidine digluconate (CHD-gluconate) are modified in many different ways and are used as antibacterial additives in cosmetics, skin disinfectants and for the treatment of wounds in veterinary medicine, as an udder disinfectant and also for disinfecting surfaces.

The composition and appearance of gluconate solutions are subject to the requirements of the European Pharmacopoeia and the American Pharmacopoeia. One of the purity requirements is a concentration of p-chloroaniline limited to 500 ppm. In a reaction which is the reverse of forming the chlorhexidine base from hexamethylenebicyanoguanidine and p-chloroaniline, p-chloroaniline can be reversibly eliminated from these solutions on dissolving the base in D(+) glucono-δ-lactone, the internal ester of D(+)-gluconic acid, wherein the solutions discolor and become increasingly yellow to brown. Decomposition of chlorhexidine solutions depends on the pH of the solution and in particular on the storage temperature. Tests show (FIG. 1), that the permissible p-chloroaniline values are exceeded after about one month when stored at a constant temperature of 40° C. Solutions of CHD-gluconate which are stable over the long-term have not hitherto been disclosed. The use of these solutions in regions with a tropical climate is therefore a problem which has not hitherto been resolved satisfactorily. Therefore, there is a need for chlorhexidine salt solutions which tend to decompose to only a small extent when used under extreme climatic conditions, in particular at high temperatures. Unfortunately, almost all the salts of chlorhexidine are sparingly soluble in water or cannot be used as human or veterinary disinfectants due to the toxicological properties of the anion. For example, the salts of chlorhexidine with hydrogen chloride, fluorophosphoric acid, bishydroxymethylpropionic acid, acetylsalicylic acid, tartaric acid, 4-hydroxybenzoic acid, 5-sulfosalicylic acid, glyoxalic acid, thioctic acid, L-malic acid, sulfanilic acid, nicotinic acid, sarcosine, L(+)-glutaminic acid, citric acid, nitrilotriacetic acid, trimethylolacetic acid, sorbic acid and many more, are sparingly soluble in water.

Although 20% aqueous solutions can be obtained with amidosulfuric acid, captopril, laevulinic acid, N-acetylglycine and S-(-)-pyrolidinone-5-carboxylic acid, these can spontaneously crystallize during inoculation or after standing for a long time. Although chlorhexidine ascorbate is very soluble in water, it is more light sensitive and more unstable than the gluconate.

SUMMARY OF THE INVENTION

Accordingly, the object of the invention is to provide storage-stable formulations which contain chlorhexidine in a water-soluble form. The formulation should be easy to prepare and should be able to be converted into aqueous chlorhexidine salt solutions. In addition, the acids required for salt production should be toxicologically harmless.

It has now been found that salts of chlorhexidine which are very soluble in water can be prepared by reacting the chlorhexidine base with the following acids or the acid lactones thereof:

Lactobionic acid (I) [CAS-No. 96-82-2], D-galactone-γ-lactone (II) [CAS-No. 2782-07-2], L-mannono-γ-lactone (III) [CAS-No. 22430-23-5], D-(-)-gulono-γ-lactone (IV) [CAS-No. 6322-07-2], D-(+)-galacturonic acid (V) [CAS-No. 91510-62-2] and α-D-heptaglucono-γ-lactone (VI) [CAS-No. 60046-25-5].

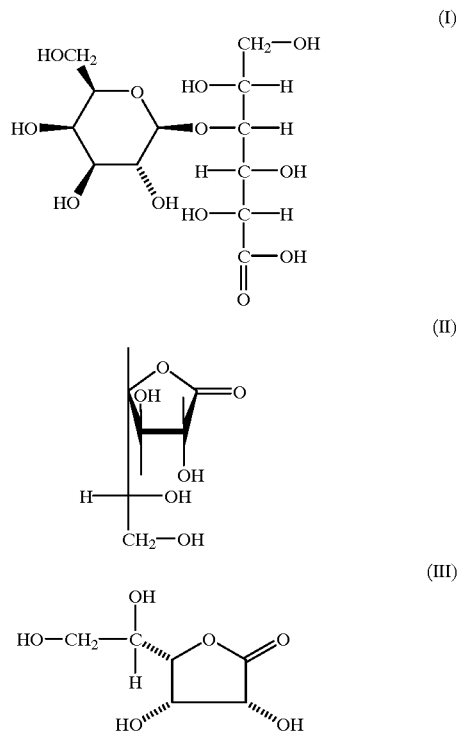

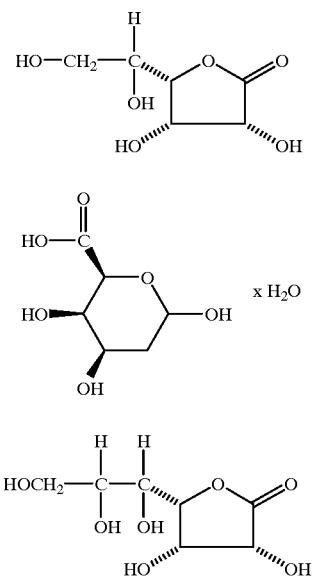

Furthermore, it was found that powdered mixtures of the chlorhexidine base with selected sugar acids or lactones thereof in accordance with the formulae (I) to (VI) and with gluconic acid or gluconolactone are substantially more stable than the readily accessible aqueous solutions of chlorhexidine salts obtained from the mixtures by dissolving in water.

The invention also provides an aqueous solution of a chlorhexidine salt with a concentration of at least 0.01 wt. %, which is characterized in that the chlorhexidine salt is selected from the set of salts of chlorhexidine with lactobionic acid (I), D-galactonic acid (II'), L-mannonic acid (III'), D-(-)-gulonic acid (IV'), D-(+)-galacturonic acid (V) and α-D-heptagluconic acid (VI'). The concentration of chlorhexidine salt is generally in the range 0.01 to 30 wt. %, in particular 1 to 20 wt. %.

Furthermore, the invention also provides new water-soluble chlorhexidine salts, characterized by the acid anion of a sugar acid from the set lactobionic acid (I), D-(+)-galacturonic acid (V), D-galactonic acid (II'), L-mannonic acid (III'), gulonic acid (IV) and α-D-heptagluconic acid (VI').

Storage trials using salt solutions according to the invention have shown that their storage stabilities are comparable to that of chlorhexidine gluconate solutions. The problem of long-term p-chloroaniline production cannot be solved by the invention of new anions. Surprisingly, however, powdered formulations according to the invention are very storage-stable; see FIGS. 1 and 2.

DETAILED DESCRIPTION OF THE INVENTION

It has now been found that chlorhexidine digluconate solutions or solutions with the sugar acid anions based on formulae (I) to (VI) which contain at least 0.01 wt. %, preferably about 20 wt. % of the particular salt but very low concentrations of p-chloroaniline can be prepared by dissolving finely powdered mixtures of chlorhexidine base with gluconic acid or gluconolactone or else with a sugar acid or its lactone of formulae (I) to (VI) in a ratio of base: acid/lactone of 1:2 to 1:>2, in particular 1:2.05 to 2.6 in the required amount of water. When using formulations with sugar acids of formulae (I), (V) or (VI) dissolution occurs within about 20 min. at room temperature by shaking the solution from time to time and, when using formulations with sugar lactones of formulae (II), (III) or (IV), by using warm water.

Figure 1:
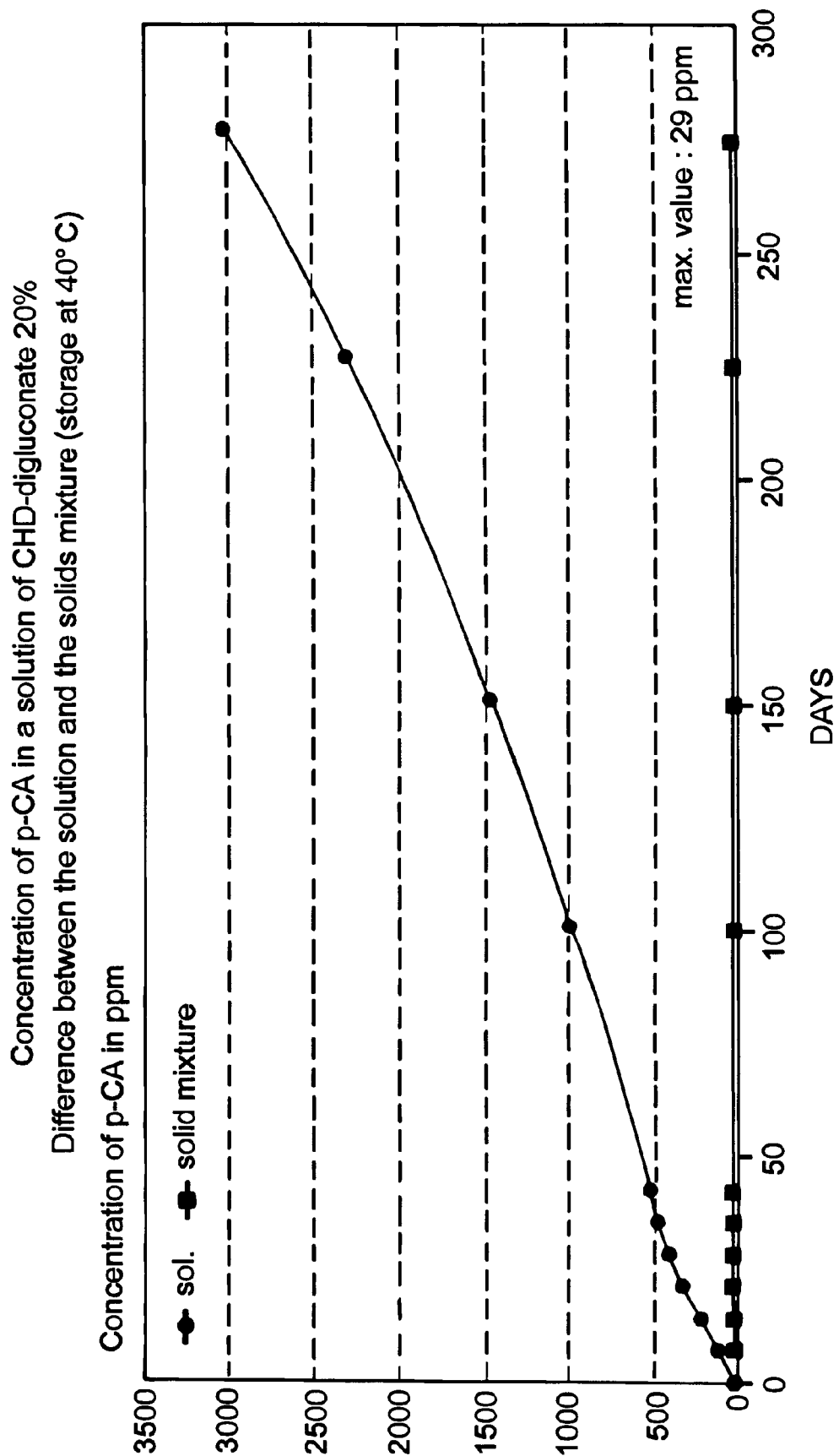
FIG. 1 shows the production of p-chloroaniline (p-CA) in aqueous 20 wt. % chlorhexidine digluconate solutions and in the corresponding powdered mixtures as a function of time.
Figure 2:
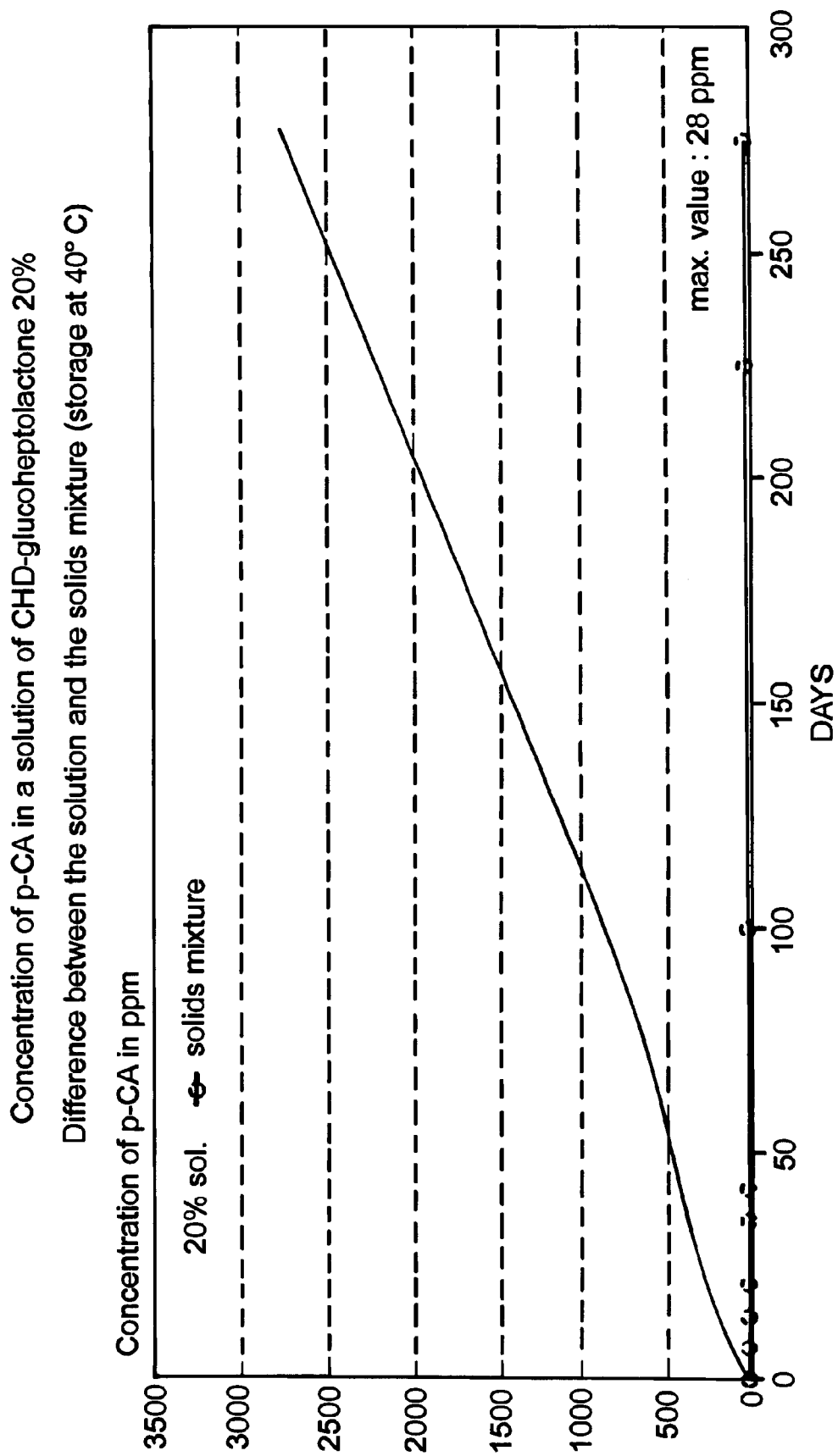
FIG. 2 shows the production of p-chloroaniline from a 20 wt. % solution of chlorhexidine-di-D-(-)-heptagluconate and from the powdered mixture containing chlorhexidine and glucoheptonic-lactone, at 40° C.

Powdered formulations according to the invention can be stored for a long period, even at elevated temperature, without p-chloroaniline being produced, as shown in FIGS. 1 and 2. In order to avoid caking of the formulations, the concentration of free water should be low, preferably less than 0.05%.

The mixtures of chlorhexidine base and a sugar acid or sugar acid lactone are obtained by careful homogenization in suitable equipment such as a tumble mixer or 'trolley' mixer followed by milling. Alternatively, it is also possible to supply the two components separately, in the theoretical ratio, to the milling device. A spiral jet mill, for example, is suitable in this case. Also, the base and acid/lactone may be milled separately and then placed in a container in the correctly adjusted stoichiometric ratio. The latter may preferably be modified in a suitable manner by filling so-called portion packs which are used once only and thus do not have to be prepared in a homogeneous form since the correct acid/lactone: base ratio is automatically produced on dissolution in water. If required, 0–10 wt. %, preferably less than 1 wt. %, of auxiliary substances such as fragrances, colorants, other disinfectants or surfactants may also be added to the formulation.

It is expedient to use the finest possible particle size for the components in order to obtain rapid dissolution. A particle size of $d_{50} < 50$ μm is preferably recommended.

It is also possible to obtain the chlorhexidine salts in crystalline form from the aqueous solutions prepared from chlorhexidine base and a sugar acid or sugar lactone. For producing the solid salt the solution is evaporated, preferably under reduced pressure. After standing for a longer time, the high-viscous mass becomes brittle and can be pulverized by crushing. In an alternative embodiment, a concentrated aqueous solution of the chlorhexidine salt is subjected to vacuum sublimation at low temperature and, in such a process, crystalline salts are obtained immediately having an instant solubility.

Formulations, solutions and chlorhexidine salts according to the invention can be used as disinfectants or to prepare disinfectants.

DETAILED DESCRIPTION OF THE PREFERRED EMBODIMENTS

EXAMPLES

1. The salt solutions are prepared by combining components (I) to (VI) with the theoretically required amount of water and chlorhexidine base.

a) Instructions for preparing aqueous 20 wt. % strength solutions of chlorhexidine salts by reacting sugar acids (I), (V) and (VI) with chlorhexidine base.

35.8 g of (I), 21.2 g of (V) or 21 g of (VI) together with 25.0 g of chlorhexidine base are added to 243 g, 185 g or 180 g respectively of water and the milky suspension which is produced is stirred for about 10–15 min. at room temperature. If required, the pH is adjusted to 5–6 by further addition of (I), (V) or (VI). Each of the resulting clear solutions contains 20 wt. % of the corresponding chlorhexidine salt.

b) Instructions for preparing aqueous 20 wt. % strength solutions of chlorhexidine salts by reacting sugar lactones (II), (III), (IV) with chlorhexidine base.

19.5 g of (II), (III) or (IV) and 25.0 g of chlorhexidine base are added to 171 g of water and the resulting suspension is heated to 60–80° C. for about 5–10 min. If required, the pH is adjusted to 5–6 by further addition of (II), (III) or (IV). Clear 20 wt. % strength solutions of the corresponding chlorhexidine salts are obtained.

2. Preparation of Chlorhexidine Salts a) 10 g of chlorhexidine base and 8,3 g of D-heptaglucono-γ-lactone were dissolved in 35 ml of water. The solution was evaporated. After standing over $P_4O_{10}$, the salt of chlorhexidine heptagluconate was obtained as a colorless crystalline mass with a melting range of 72 to 76° C.

b) In analogous manner, other chlorhexidine(CH)-salts have the below cited melting ranges.
CH-lactobionate 100–115° C.
CH-galacturonate 118–125° C.
CH-galactonate 140–145° C.

What is claimed is:

1. A storage-stable powdered chlorhexidine base formulation comprising:
   a water soluble mixture of chlorhexidine base and one or more sugar acids or lactones of sugar acids, the one or more sugar acids being selected from the group consisting of gluconic acid, gluconolactone, lactobionic acid (I), D-galactono-γ-lactone (II), L-mannono-γ-lactone (III), D-(−)-gulono-γ-lactone (IV), D-(+)-galacturonic acid (V) and α-D-heptaglucono-γ-lactone (VI), wherein the molar ratio of chlorhexidine base to sugar acid or lactone of a sugar acid is 1 to greater than or equal to 2;
   less than 0.05% free water; and
   0 to 10 wt. % of auxiliary substances;
   wherein the storage-stable, powdered chlorhexidine formulation comprises less than 500 ppm p-chloroaniline after 250 days in storage.

2. A formulation according to claim 1, wherein the molar ratio of chlorhexidine base to sugar acid or lactone thereof is 1:2.05 to 2.6 and the concentration of auxiliary substances is less than 1 wt. %.

3. The storage-stable, powdered chlorhexidine formulation of claim 1, wherein the storage-stable, powdered chlorhexidine formulation comprises less than 500 ppm p-chloroaniline after at least 250 days of storage at 40° C.

4. The storage-stable, powdered chlorhexidine formulation of claim 3, wherein the storage-stable, powdered chlorhexidine formulation comprises less than 30 ppm p-chloroaniline after at least 250 days of storage.

5. The storage-stable, powdered chlorhexidine formulation of claim 1, wherein the storage-stable, powdered chlorhexidine formulation comprises less than 30 ppm p-chloroaniline after at least 250 days of storage.

6. A storage-stable powdered chlorhexidine base formulation comprising:
   a water soluble mixture of chlorhexidine base and one or more sugar acids or lactones of sugar acids, the sugar acid being selected from the group consisting of gluconic acid, gluconolactone, lactobionic acid (I), D-galactono-γ-lactone (II), L-mannono-g-lactone (III), D-(−)-gulono-γ-lactone (IV), D-(+)-galacturonic acid (V) and α-D-heptaglucono-γ-lactone (VI), wherein the molar ratio of chlorhexidine base to sugar acid or lactone of a sugar acid ranges from 1:2 to 1:2.6;
   less than 0.05% free water; and
   0 to 10 wt. % of auxiliary substances;
   wherein the storage-stable powdered chlorhexidine formulation contains less than 30 ppm p-chloroaniline after 250 days in storage at 40° C.

* * * * *